United States Patent
Yeshurun et al.

(10) Patent No.: US 11,357,740 B2
(45) Date of Patent: *Jun. 14, 2022

(54) CANNABIDIOL FOR ENHANCING THE THERAPEUTIC EFFECT OF A STEROID

(71) Applicant: STERO BIOTECHS LTD., Ramat Gan (IL)

(72) Inventors: Moshe Yeshurun, Elqana (IL); Sari Prutchi Sagiv, Ramat Gan (IL)

(73) Assignees: STERO BIOTECHS LTD., Ramat Gan (IL); MOR RESEARCH APPLICATIONS LTD., Tel Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/048,856

(22) Filed: Jul. 30, 2018

(65) Prior Publication Data

US 2018/0333370 A1 Nov. 22, 2018

Related U.S. Application Data

(63) Continuation of application No. 15/877,665, filed on Jan. 23, 2018, now Pat. No. 10,058,515, which is a continuation of application No. 15/143,694, filed on May 2, 2016, now Pat. No. 9,889,100, which is a continuation-in-part of application No. 14/787,515, filed as application No. PCT/IL2014/050385 on Apr. 29, 2014, now Pat. No. 9,956,182.

(60) Provisional application No. 61/818,525, filed on May 2, 2013.

(51) Int. Cl.
*A61K 31/05* (2006.01)
*A61K 9/14* (2006.01)
*A61K 45/06* (2006.01)
*A61K 9/00* (2006.01)

(52) U.S. Cl.
CPC ............ *A61K 31/05* (2013.01); *A61K 9/0014* (2013.01); *A61K 9/0053* (2013.01); *A61K 45/06* (2013.01); *A61K 9/0095* (2013.01)

(58) Field of Classification Search
USPC ........................................................ 514/279
See application file for complete search history.

(56) References Cited

U.S. PATENT DOCUMENTS

| 6,410,588 B1 | 6/2002 | Feldmann et al. | |
|---|---|---|---|
| 7,759,526 B2 | 7/2010 | Mechoulam et al. | |
| 2011/0195096 A1* | 8/2011 | Kindler | A61K 31/20 424/400 |

FOREIGN PATENT DOCUMENTS

| WO | 0195899 A2 | 12/2001 |
|---|---|---|
| WO | 2008107879 A1 | 9/2008 |
| WO | 2013025984 A2 | 2/2013 |

OTHER PUBLICATIONS

Bhattacharyya S. et al. "Opposite Effects of Δ-9-Tetrahydrocannabinol and Cannabidiol on Human Brain Function and Psychopathology" Neuropsychopharmacology 35:764-774 (2010).
Bisogno T, et al. Molecular targets for cannabidiol and its synthetic analogues: effect on vanilloid VR1 receptors and on the cellular uptake and enzymatic hydrolysis of anandamide. Br J Pharmacol. 134(4):845-52 (2001).
D'Souza D. et al., "Blunted Psychotomimetic and Amnestic Effects of Δ-9-Tetrahydrocannabinol in Frequent Users of Cannabis" Neuropsychopharmacology 33:2505-2516 (2008).
Farrimond et al., "Cannabinol and cannabidiol exert opposing effects on rat feeding patterns" Psychopharmacology, 223(1):117-129 (2012).
Fasinu et al., "Current Status and Prospects for Cannabidiol Preparations as New Therapeutic Agents" Pharmacotherapy 36(7):781-796 (2016).
Guimares et al., "Antianxiety effect of cannabidiol in the elevated plus-maze" Psychopharmacology 100:558-559 (1990).
Lam et al., "Characterization and comparison of recombinant human and rat TRPV1 receptors: effects of exo- and endocannabinoids" British Journal of Anaesthesia, 94(5):649-656 (2005).
Ligresti et al., "Antitumor activity of plant cannabinoids with emphasis on the effect of cannabidiol on human breast carcinoma," Journal of Pharmacology and Experimental Therapeutics, 318(3):1375-87 (2006).
Malfait et al., "The nonpsychoactive cannabis constituent cannabidiol is an oral anti-arthritic therapeutic in murine collagen-induced arthritis" PNAS 97(17):9561-9566 (2000).
Pertwee., "Commentary GPR55: a new member of the cannabinoid receptor clan?" British Journal of Pharmacology, 152(7):984-986 (2007).
Pertwee, The diverse CB1 and CB2 receptor pharmacology of three plant cannabinoids: Δ9-tetrahydrocannabinol, cannabidiol and Δ9-tetrahydrocannabivarin British Journal of Pharmacology, 153(3):199-215 (2008).
Petrocellis et al., Non-THC cannabinoids inhibit prostate carcinoma growth in vitro and in vivo: pro-apoptotic effects and underlying mechanisms British Journal of Pharmacology, 168(91):79-102 (2013).
Ram et al., "Prophylaxis regimens for GVHD: systematic review and meta-analysis" Bone Marrow Transplantation 43, 643-653 (2009).
Shinjyo et al., "The effect of cannabichromene on adult neural stem/progenitor cell" Neurochemistry International, 63(5):432-437 (2013).
Srivastava et al., 9 Tetrahydrocannabinol and cannabidiol alter cytokine production by human immune cells Immunopharmacology 40:179-185 (1998).
Szallasi et al., "Vanilloid (Capsaicin) Receptors and Mechanisms" Pharmacological Reviews 51(2) 159-211 (1999).
Zygmunt, et al. Vanilloid receptors on sensory nerves mediate the vasodilator action of anandamide. Nature, (400):452-7 (1999).

(Continued)

*Primary Examiner* — Kathrien A Cruz
(74) *Attorney, Agent, or Firm* — The Roy Gross Law Firm, LLC; Roy Gross

(57) ABSTRACT

The invention provides methods for preventing, ameliorating and treating the acute and chronic forms of graft-versus-host disease (GVHD) by using Cannabidiol compositions.

16 Claims, No Drawings

(56) References Cited

OTHER PUBLICATIONS

Antin., "Acute graft-versus-host disease: inflammation run amok?" The Journal of Clinical Investigation, 107 (12):1497-1498 (2001).

Borrelli et al., "Cannabidiol, a safe and non-psychotropic ingredient of the marijuana plant Cannabis sativa, is protective in a murine model of colitis" J Mol Med 87:1111-1121 (2009).

Carrier et al., "Inhibition of an equilibrative nucleoside transporter by cannabidiol: A mechanism of cannabinoid immunosuppression" PNAS 103(20):7895-7900 (2006).

Choi et al., "Pathogenesis and Management of Graft versus Host Disease" Immunol Allergy Clin North Am 30(1):75-101 (2010).

Keeble et al., "Involvement of transient receptor potential vanilloid 1 in the vascular and hyperalgesic components of joint inflammation" Arthritis Rheum. Oct.;52(10):3248-56 (2005) (Abstract Only).

Kim et al., "Induction of Lethal Graft-versus-Host Disease by Anti-CD137 Monoclonal Antibody in Mice Prone to Chronic Graft-versus-Host Disease," Biol Blood Marrow Transplant 15: 306-314 (2009).

Kozela et al., "Cannabidiol inhibits pathogenic T cells, decreases spinal microglial activation and ameliorates multiple sclerosis-like disease in C57BL/6 mice" British Journal of Pharmacology 163:1507-1519 (2011).

Kozela et al., "Cannabinoids Decrease the Th17 Inflammatory Autoimmune Phenotype" J Neuroimmune Pharmacol 8(5):1265-76 (2013).

Lee et al., "A comparative study on cannabidiol-induced apoptosis in murine thymocytes and EL-4 thymoma cells" Int Immunopharmacol. 8(5):732-40 (2008) (Abstract Only).

Szabo et al., "Role of Transient Receptor Potential Vanilloid 1 Receptors in Adjuvant-Induced Chronic Arthritis: In Vivo Study Using Gene-Deficient Mice" The Journal of Pharmacology and Experimental Therapeutics314(1):111-119 (2005).

Liddle, "The Role of Transient Receptor Potential Vanilloid 1 (TRPV1) Channels in Pancreatitis" Biochim Biophys Acta. 1772(8): 869-878 (2007).

McHugh et al., "Inhibition of Human Neutrophil Chemotaxis by Endogenous Cannabinoids and Phytocannabinoids: Evidence for a Site Distinct from CB1 and CB2" Mol Pharmacol 73:441-450 (2008).

Mechoulam et al., "Cannabidiol—Recent Advances" Chemistry & Biodiversity, 4:1678-1692 (2007).

Mielcarek et al., "Prognostic relevance of 'early-onset' graft-versus-host disease following non-myeloablative haematopoietic cell transplantation" British Journal of Haematology, 129:381-391 (2005).

Atakan, "Cannabis, a complex plant: different compounds and different effects on individuals," Ther Adv Psychopharmacol 2:241-254 (2012).

Rieder et al., "Cannabinoid-induced apoptosis in immune cells as a pathway to immunosuppression" Immunobiology. 215(8): 598-605 (2010).

Sido et al., "Δ9-Tetrahydrocannabinol attenuates allogeneic host-versus-graft response and delays skin graft rejection through activation of cannabinoid receptor 1 and induction of myeloid-derived suppressor cells" Journal of Leukocyte Biology 98(3):435-447 (2015).

Administrator (Medicinal Cannabinoid FAQ: What are THC, CBD, CBN, CBC and . . . ?, Dec. 12, 2011, pp. 1-3).

Nagarkatti, M. et al., "Do Cannabinoids have a therapeutic role in transplantation?", Trends in Pharmacological Sciences, Jun. 28, 2010, pp. 345-350, vol. 31, Issue: 8.

Pandey, R., et al., "Targeting Cannabinoid Receptors as a Novel Approach in the Treatment of Graft-versus-Host Disease: Evidence from an Experimental Murine Model", Journal of Pharmacology and Experimental Therapeutics, Sep. 2011, pp. 819-828, vol. 338, Issue: 3, USA.

"Safety and Efficacy of Cannabidiol for Grade I/II Acute Graft Versus Host Disease (GVHD) After Allogeneic Stem Cell Transplantation" Published Online: Sep. 9, 2012. URL: https://trialbulletin.com/lib/entry/ct-01596075.

Lee, S. J., et al., "Chronic Graft-versus-Host Disease", Biology of Blood and Marrow Transplantation, Apr. 2003, pp. 215-233, vol. 9, Issue: 4.

Champlin, R. E., et al., "Blood stem cells compared with bone marrow as a source of hematopoietic cells for allogeneic transplantation. IBMTR Histocompatibility and Stem Cell Sources Working Committee and the European Group for Blood and Marrow Transplantation", Blood, 2000, pp. 3702-3709, vol. 95.

Castro-Malaspina, H., et al. "Unrelated donor marrow transplantation for myelodysplastic syndromes: outcome analysis in 510 transplants facilitated by the National Marrow Donor Program", Blood, Mar. 2002, pp. 1943-1951, vol. 99, Issue 6.

McGlave, P. B., et al., "Unrelated donor marrow transplantation for chronic myelogenous leukemia: 9 years' experience of the National Marrow Donor Program", Blood, 2000, pp. 2219-2225, vol. 95, Issue: 7.

Jagasia, M., et al., "Risk factors for acute GVHD and survival after hematopoietic cell transplantation", Blood, Jan. 2012, pp. 296-307, vol. 119, Issue 1.

Flowers, M. E. D., et al., "Comparative analysis of risk factors for acute graft-versus-host disease and for chronic graft-versus-host disease according to National Institutes of Health consensus criteria", Blood, Mar. 2011, pp. 3214-3219, vol. 117, Issue 11.

Pavletic, S. Z., et al., "Influence of T-cell depletion on chronic graft-versus-host disease: results of a multicenter randomized trial in unrelated marrow donor transplantation", Blood, Nov. 2005, pp. 3308-3313, vol. 106, Issue 9.

Arai S., et al., "Poor outcome in steroid-refractory graft-versus-host disease with antithymocyte globulin treatment", Biology of Blood and Marrow Transplantation, 2002, pp. 155-160, vol. 8, Issue 3.

Westin, J. R., et al., "Steroid-Refractory Acute GVHD: Predictors and Outcomes", Advances in Hematology, 2011, pp. 1-8, vol. 2011.

Joachim Deeg, H., "How I treat refractory acute GVHD", Blood, May 2007, pp. 4119-4126, vol. 109, Issue 10.

Jacobsohn, D. A., et al., "Review: Acute graft versus host disease", Orphanet Journal of Rare Diseases, Sep. 2007, vol. 2, Issue 35.

Martin P.J., "A Retrospective Analysis of Therapy for Acute Graft-Versus-Host Disease: Initial Treatment", Blood, Oct. 1990, pp. 1464-1472, vol. 76, Issue 8.

Ben-Shabat S. et al. "New Cannabidiol Derivatives: Synthesis, Binding to Cannabinoid Receptor, and Evaluation of Their Antiinflammatory Activity", J. Med. Chem. 2006, 49, 1113-1117 (6 pages).

Raphael Mechoulam et al., "Cannabidiol: an overview of some chemical and pharmacological aspects. Part I: chemical aspects", Chemistry and Physics of Lipids 121 (2002) 35/43 (9 pages).

Dennis B. Leveson-Gower et al., "Mast cells suppress murine GVHD in a mechanism independent of CD4 +CD25+ regulatory T cells", Blood 2013 122(22):3659-3665 (6 pages).

Bertin S. et al., "The ion channel TRPV1 (vanilloid receptor) regulates the activation and proinflammatory properties of CD4+ T cells", Nat Immunol. Nov. 2014; 15(11): 1055-1063. doi:10.1038/ni.3009 (33 pages).

https://www.clinicaltrials.gov/ct2/show/NCT01385124 date: Jun. 28, 2011 "Cannabidiol for Graft Versus Host Disease (GVHD) Prophylaxis in Allogeneic Stem Cell Transplantation" (3 pages).

Cahn J.Y. et al, "Prospective evaluation of 2 acute graft-versus-host (GVHD) grading systems", Blood, Aug. 2005, pp. 1495-1500, vol. 106, Issue 4.

Filipovich A.H. et al, "National Institutes of Health Consensus Development Project on Criteria for Clinical Trials in Chronic Graft-versus-Host Disease: I. Diagnosis and Staging Working Group Report", Biology of Blood and Marrow Transplantation, 2005, pp. 945-955, vol. 11.

Weiss et al., "Cannabidiol lowers incidence of diabetes in nonobese diabetic mice"; Autoimmunity; vol. 39 (2): pp. 143-151, Mar. 2006.

International Search Report from a counterpart foreign application—PCT/IL2014/050385—5 pages, dated Aug. 10, 2014.

Written Opinion of the International Searching Authority from a counterpart foreign application—PCT/IL2014/050385—7 pages, dated Aug. 10, 2014.

* cited by examiner

CANNABIDIOL FOR ENHANCING THE THERAPEUTIC EFFECT OF A STEROID

CROSS-REFERENCE TO RELATED APPLICATIONS

This is a continuation of U.S. patent application Ser. No. 15/877,665, filed on Jan. 23, 2018, which is a continuation of U.S. patent application Ser. No. 15/143,694, filed on May 2, 2016, which is a continuation-in-part of U.S. patent application Ser. No. 14/787,515, filed on Oct. 28, 2015, which is a national phase of PCT Patent Application No. PCT/IL2014/050385, filed on Apr. 29, 2014, which claims the benefit of priority of U.S. Provisional Patent Application No. 61/818,525, filed on May 2, 2013. The foregoing patent applications are incorporated by reference in their entirety herein.

FIELD

The present invention relates to methods and uses of Cannabidiol compositions in steroid therapy and in the treatment of the severe and refractory forms of acute and chronic graft-versus-host disease (GVHD), and conditions associated therewith.

BACKGROUND

Graft-versus-host disease (GVHD) is among the most frequent complication of allogeneic hematopoietic stem cell transplantation (HSCT) and is associated with significant morbidity and mortality. Mortality rates as a direct or indirect consequence of GVHD can reach 50% despite the prophylactic use of immunosuppressive drugs like cyclosporine, tacrolimus, ATG, methotrexate, and mycophenolate mofetil which are administered for prevention of GVHD.

Two distinct types of GVHD are clinically recognized, acute and chronic. The acute form of the disease usually develops within the first three months after transplantation. The incidence rate of acute GVHD is estimated at 30-50% among patients receiving transplant from HLA-identical sibling donors, and 50-70% in patients receiving HLA-matched unrelated transplants. Severe acute GVHD (grade III-IV) occurs in up to 20% of recipients of related donors (Champlin, Blood 2000; 95:3702-3709) and up to 35% of unrelated donors (Castro-Malaspina, Blood 2002; 99:1943-1951, McGlave, Blood 2000; 95:2219-2225, Jagasia, Blood 2012; 119:296-307). Severe acute GVHD carries a poor prognosis, with 25% long term survival for grade III and 5% for grade IV (Cahn et al, 2005).

Chronic GVHD occurs in up to 60% of patients receiving HLA-identical sibling marrow grafts and 70% of patients receiving alternative donor marrow grafts who survive beyond day 100. (Lee, BBMT 2003; 9: 215-233). Symptoms of chronic GVHD usually present between 3 months and 2 years after allogeneic transplantation, and about two thirds develop within the first 12 months. Altogether, only less than 20% of transplanted patients do not develop either acute or chronic GVHD (Flowers, Blood 2011; 117(11): 3214-3219).

It is well accepted that acute and chronic GVHD are unique different processes. This fact is emphasized by the observations that chronic GVHD can occur without prior acute GVHD, and that interventions that are successful in preventing or treating acute GVHD most commonly fail to decrease chronic GVHD (Pavletic, Blood 2005; 106:3308-3313, Thomas hematopietic cell transplantation, $4^{th}$ edition, page 1307, Wiley-Blackwell). Most investigators now consider chronic GVHD as a disease of immune dysregulation that involves donor-derived immune cells and host cell populations and tissues. This process is likely initiated by donor-derived T cells and is both alloreactive (directed against the recipient's histocompatibility antigens) and autoreactive (directed against antigens present on both the donor and recipient). The activated immune response then proceeds unchecked by the thymic or peripheral mechanisms of deletion and immunoregulation. Critical donor or recipient tolerance-promoting mechanisms may be absent.

Conventional treatment of chronic GVHD requires prolonged periods of systemic immunosuppressive therapy; however these treatments have limited effectiveness, and very often cause severe adverse effects.

Thus, developing innovative strategies to treat GVHD, such as the severe forms that most often lead to mortality, is a major unmet need.

SUMMARY

According to one aspect the present invention there is provided a method of preventing, ameliorating or treating graft-versus-host disease (GVHD) in a subject in need thereof. The method comprises the step of administering to the subject a therapeutically effective amount of Cannabidiol or any derivative thereof. In some embodiments, the subject is a patient undergoing transplantation. According to a specific embodiment, the subject is a patient undergoing allogeneic hematopoietic stem cell transplantation.

In some embodiments, the allogeneic hematopoietic stem cells transplanted in the subject are received from a sibling or an unrelated donor, from bone marrow or peripheral blood hematopoietic stem cell grafts. Alternative sources of hematopoietic stem cells grafts are cord blood units, haploidentical peripheral blood or bone marrow stem cells.

According to some embodiments of the invention, Cannabidiol, or any derivative thereof, is administered to a patient before and or after transplantation. In some specific embodiments the method may further comprise the step of administering of at least one additional therapeutic agent. In some embodiments, Cannabidiol, or any derivative thereof, is administered orally in doses of between about 0.5 mg to about 600 mg each administration once to three times daily.

According to another aspect there is provided a pharmaceutical composition for preventing or treating GVHD comprising Cannabidiol or any derivative thereof, and a pharmaceutically acceptable carrier.

According to yet another aspect there is provided Cannabidiol or any derivative thereof, for use in the prevention and treatment of the GVHD in a subject.

According to yet another aspect there is provided a method for treating a subject afflicted with a condition associated with acute graft versus host disease (GVHD) or chronic GVHD, comprising administering to the subject a therapeutically effective amount of a composition comprising a cannabidiol (CBD) or a functional derivative thereof.

According to yet another aspect there is provided a method for enhancing the therapeutic effect of a steroid in a subject in need of a steroid therapy, comprising administering to the subject the steroid and a cannabidiol (CBD) or a functional derivative thereof.

DETAILED DESCRIPTION

Described herein is the surprising observation that administration of a composition comprising Cannabidiol or a functional derivative thereof to transplanted patients experiencing the symptoms of, and diagnosed with severe forms of acute and chronic graft-versus-host-disease (GVHD), showed significant improvement in the disease severity, halted disease progression and even complete remission of its symptoms. Accordingly, provided herein are methods for the treatment GVHD and its symptoms, in its severest forms, by administration of CBD to a subject in need thereof.

I. Graft Versus Host Disease

Graft-versus-host-disease (GVHD) is a life-threatening, complication that can arise following allogeneic hematopoietic cell transplantation. GVHD is the leading cause of post-transplantation morbidity and non-relapse mortality in hematopoietic stem cell transplants (HSCTs), and poses the greatest threat to transplantation success (Pasquini and Wang, 2013).

There are two main categories of GVHD, each with two subcategories as outlined in Table 1, below. The broad category of acute GVHD includes (1) classic acute GVHD (maculopapular rash, nausea, vomiting, anorexia, profuse diarrhea, ileus, or cholestatic hepatitis) occurring within 100 days after transplantation or Donor Lymphocyte Infusion (DLI) without diagnostic or distinctive signs of chronic GVHD, and (2) persistent, recurrent, or late-onset acute GVHD (features of classic acute GVHD without diagnostic or distinctive manifestations of chronic GVHD) occurring beyond 100 days of transplantation or DLI (often seen after withdrawal of immune suppression).

The broad category of chronic GVHD includes (1) classic chronic GVHD without features characteristic of acute GVHD and (2) an overlap syndrome in which features of chronic and acute GVHD appear together. In the absence of histologic or clinical signs or symptoms of chronic GVHD, the persistence, recurrence, or new onset of characteristic skin, GI tract, or liver abnormalities should be classified as acute GVHD regardless of the time after transplantation. With appropriate stratification, patients with persistent, recurrent, or late-onset acute GVHD or overlap syndrome can be included in clinical trials with patients who have chronic GVHD (Filipovich et al, 2005).

TABLE 1

Categories of Acute and Chronic GVHD

| Category | Time of symptoms after HCT or DLI | Presence of aGVHD features | Presence of cGVHD features |
|---|---|---|---|
| Acute GVHD | | | |
| Classic aGVHD | ≤100 d | Yes | No |
| Persistent, recurrent or late-onset aGVHD | >100 d | Yes | No |
| Chronic GVHD | | | |
| Classic cGVHD | No time limit | No | Yes |
| Overlap syndrome | No time limit | Yes | Yes |

Adapted from Filipovich et al, 2005

Acute GVHD

Clinically, acute GVHD, treated by the methods described herein, is suspected when a recipient of HSCT develops any or all of the following signs or symptoms: dermatitis (skin rash), cutaneous blisters, crampy abdominal pain with or without diarrhea, persistent nausea and vomiting, or hepatitis (with elevation of bilirubin and/or liver enzymes). Typically, these symptoms start with donor engraftment and may occur up to day 100 after the HSCT, but may also occur later. Acute GVHD is a clinical diagnosis but, as many the symptoms of acute GVHD are non-specific, histologic confirmation, especially if the symptoms are atypical or involve just the liver or gut, may be extremely useful (Jacobsohn & Voselsang, 2007).

As shown in Table 2, the clinical manifestations (also described herein as the "associated conditions" or "associated symptoms") of acute GVHD occur in the skin, gastrointestinal tract and liver (Vogelsang et al, 2003). In a comprehensive review, Martin et al found that at the onset of acute GVHD, 81% of patients had skin involvement, 54% had GI involvement, and 50% had liver involvement (Martin et al, 1990).

TABLE 2

Acute GVHD symptoms

| | |
|---|---|
| Skin | Maculopapular skin rash |
| Upper GI tract | Nausea and/or anorexia + positive histology |
| Lower GI tract | Watery diarrhea ≥500 mL ± severe abdominal pain ± bloody diarrhea or ileus (after exclusion of infectious etiology) |
| Liver | Cholestatic hyperbilirubinemia |

Adapted from Ferrara et al, 2009

The incidence of the severity of acute GVHD is determined by the extent of involvement of the three principal target organs (see Table 2 above). The overall characteristics of the stages and grades of acute GVHD (aGVHD) are listed in
Table 3 (Jacobsohn & Voselsang, 2007). Severe acute GVHD carries a poor prognosis, with 25% long term survival for grade III and 5% for grade IV (Cahn et al, 2005).

TABLE 3

Skin, liver and GI characteristics of the stages and grades of aGVHD

| Stage | Skin | Liver (bilirubin) | Gut (stool output/day) |
|---|---|---|---|
| 0 | No GVHD rash | <2 mg % | <500 mL/day or persistent nausea |
| 1 | Maculopapular rash <25% BSA | 2-3 mg % | 500-999 mL/day |
| 2 | Maculopapular rash 25-50% BSA | 3.1-6 mg % | 1000-1500 mL/day |
| 3 | Maculopapular rash >50% BSA | 6.1-15 mg % | Adult: >1500 mL/day |
| 4 | Generalized erythroderma + bullous formation | >15 mg % | Severe abdominal pain with or without ileus |
| Grade | | | |
| I | Stage 1-2 | None | None |
| II | Stage 3 or (go to next column) | Stage 1 or (go to next column) | Stage 1 |
| III | — | Stage 2-3 or (go to next column) | Stage 2-3 |
| IV | Stage 4 or (go to next column) | Stage 4 | — |

Adapted from Jacobsohn & Voselsang, 2007

Treatments for Acute GVHD

Corticosteroids remain the standard first-line treatment for patients who fail prevention and develop acute GVHD. The majority of centers use methylprednisolone (MP) at doses of 1-2 mg/kg body weight. The present invention, in some embodiment, combines treatment with a steroid such as MP with Cannabidiol or a functional derivative thereof. The response to primary treatment is of central importance since responses correlate with survival. Patients not responding to steroids have a dismal prognosis. It will be appreciated that clinical definitions change over time, however, the current definition of nonresponse or refractoriness to first line aGVHD therapy is: progression after 3 days, no improvement after 7 days, or incomplete response after 14 days. Patients refractory to first line therapy are offered second-line treatment. However, there is no standard second-line treatment for acute GVHD. Widely used components are MMF, anti-TNF antibodies, other monoclonal antibodies, ATG, extracorporeal photopheresis, MTX and mesenchymal stem cells. Despite partial or complete response rates of 35%-70% with second-line medications, survival at 6-12 months is dismal, only 30%. As described further herein, the current disclosure relates to administration of CBD and derivatives thereof to subjects that have aGVHD, including severe aGVHD. Such patients include those classified as having Grade III or Grade IV GVHD, and/or patients who are refractory to other treatments. In one embodiment, refractory GVHD is steroid refractory GVHD—the steroid treatment does not treat, ameliorate or improve a clinical outcome or a clinical score in a subject afflicted with GVHD. In one embodiment, steroid refractory GVHD is characterized by deterioration in at least one GVHD symptom or a condition associated with GVHD as further described herein. In one embodiment, steroid refractory GVHD is characterized by deterioration in at least one GVHD symptom or a condition associated with GVHD after 2 days of a steroid treatment. In one embodiment, steroid refractory GVHD is characterized by deterioration in at least one GVHD symptom or a condition associated with GVHD after 3 days of a steroid treatment. In one embodiment, steroid refractory GVHD is characterized by deterioration in at least one GVHD symptom or a condition associated with GVHD after 4 days of a steroid treatment. In one embodiment, steroid refractory GVHD is characterized by deterioration in at least one GVHD symptom or a condition associated with GVHD after 5 days of a steroid treatment. In one embodiment, steroid refractory GVHD is characterized by deterioration in at least one GVHD symptom or a condition associated with GVHD after 6 days of a steroid treatment.

In one embodiment, steroid refractory GVHD is characterized by lack of improvement in at least one GVHD symptom or a condition associated with GVHD after 4 to 10 days of a steroid treatment. In one embodiment, steroid refractory GVHD is characterized by lack of improvement in at least one GVHD symptom or a condition associated with GVHD after 5 to 9 days of a steroid treatment. In one embodiment, steroid refractory GVHD is characterized by lack of improvement in at least one GVHD symptom or a condition associated with GVHD after about (±2 days) 7 days of a steroid treatment.

In one embodiment, steroid refractory GVHD is characterized by lack of remission in GVHD and/or at least one GVHD symptom or a condition associated with GVHD after 8 to 21 days of a steroid treatment. In one embodiment, steroid refractory GVHD is characterized by lack of remission in GVHD and/or at least one GVHD symptom or a condition associated with GVHD after 10 to 18 days of a steroid treatment. In one embodiment, steroid refractory GVHD is characterized by lack of remission in GVHD and/or at least one GVHD symptom or a condition associated with GVHD after 12 to 16 days of a steroid treatment. In one embodiment, steroid refractory GVHD is characterized by lack of remission in GVHD and/or at least one GVHD symptom or a condition associated with GVHD after about (±2 days) 14 days of a steroid treatment.

Chronic Graft-Versus-Host-Disease

Chronic GVHD is distinctive from acute GVHD and is not simply an evolution of acute GVHD. Chronic GVHD is a syndrome of variable clinical features resembling autoimmune and other immunologic disorders such as scleroderma. The pathophysiology of the chronic GVHD syndrome may involve inflammation, cell-mediated immunity, humoral immunity, and fibrosis. Clinical manifestations nearly always present during the first year after transplantation, but some cases develop many years after HCT. Manifestations of chronic GVHD may be restricted to a single organ or site or may be widespread, with profound impact on quality of life.

Global Scoring of Chronic GVHD

Similar to the aGVHD "Grade" classification, Chronic GVHD severity score at baseline predicts overall survival and non-relapse mortality. The methods of the present invention, in some embodiment, enhances overall survival and/or reduces non-relapse mortality of a subject afflicted with GVHD.

Eight organs or sites (skin, mouth, eyes, gastrointestinal tract, liver, lungs, joint and fascia, and genital tract) are considered for calculating global score. The methods of the present invention, in some embodiment, treat the different global scores and the various organs involved in the GVHD. Elements included in the proposed global scoring include both the number of organs or sites involved and the severity score within each affected organ. The global descriptions of mild, moderate, and severe were chosen to reflect the degree of organ impact and functional impairment due to chronic GVHD. Although scoring is often used at the time of initial diagnosis, evaluating the clinical score periodically during the course of chronic GVHD may revise prognostic expectations and better describe the current severity of chronic GVHD. Mild chronic GVHD, treated by the current methods, is present when one or two organs show symptoms with no more than a score of 1 plus, and the lung score is 0. Moderate chronic GVHD, treated by the current methods, is present when three or more organs are involved with a score of 1 OR at least one organ is involved with a score of 2 or the lung score is 1. Lastly, severe chronic GVHD, treated by the current methods, is present when at least one organ has a score of 3 OR the lung score is 2 or 3.

Symptomatic mild chronic GVHD, treated by the current methods, may be managed with local therapies alone (e.g. topical corticosteroids for the skin involvement) and CBD or any functional derivative thereof. In patients with chronic GVHD that involves three or more organs or with a score of 2 or greater in any single organ, however, systemic immunosuppressive therapy is administered together with CBD or any functional derivative thereof. In some examples however, some organ sites (mouth, eyes, genital tract), aggressive local therapy alone may be reasonable together with CBD or any functional derivative thereof, as response to systemic therapy may be suboptimal or may not warrant the risk of treatment. Early intervention with effective systemic therapy together with CBD or any functional derivative thereof can treat or prevent progression to severe chronic GVHD or the treatment and/or escalation of severe chronic GVHD. Effective immune-modulating therapy together with CBD or any functional derivative thereof can ameliorate clinical manifestations and possibly prolong survival. In patients with newly diagnosed chronic GVHD already taking immune suppressive medications a CBD or any functional derivative thereof may further enhance the efficacy of treatment.

Chronic GVHD, treated by the present methods, is one of the major causes of late treatment related mortality (TRM) after allogeneic HCT. Prospective studies have shown that the skin score, lung score, and gastrointestinal score each predict the risk of TRM. Previous studies have identified several factors associated with an increased risk of TRM among patients with chronic GVHD, including involvement of multiple organs or sites, decreased clinical performance score, thrombocytopenia at the time of diagnosis, progressive onset of chronic GVHD from prior acute GVHD (or onset of chronic GVHD during steroid treatment), hyperbilirubinemia, a higher percentage of skin involvement at the time of diagnosis, and others. Characteristics consistently associated with an increased risk of late TRM among patients with chronic GVHD are thrombocytopenia and progressive onset of chronic GVHD from acute GVHD.

Treatments for Chronic GVHD

Current treatments for chronic GVHD seek to relieve symptoms, control disease activity, and prevent damage and disability, but the efficacy of currently-used local and/or systemic is mixed, with patients often refractory to treatment. In the current disclosure, it is shown that administration of cannabidiol to patients with severe refractory chronic GVHD experienced dramatic improvement, and in certain examples complete remission, of the GVHD as observable in treatment of the symptoms and related conditions.

II. CBD Treatment of GVHD

According to one aspect, the present invention provides pharmaceutical compositions comprising CBD or any functional derivative thereof for use in methods of treating acute and/or chronic GVHD. In some embodiments, the invention provides a method for treating Grade III and/or Grade IV acute GVHD with a pharmaceutical composition of the invention. In some embodiments, the invention provides a method for treating severe chronic GVHD with a pharmaceutical composition of the invention.

The compositions specified herein below, comprise Cannabidiol (CBD), or any functional derivative thereof (i.e. a CBD derivative possessing similar, equivalent, or increased efficacy). In some embodiments, the described compositions optionally further comprise at least one pharmaceutically acceptable carrier, diluent, excipient and/or additive.

The phrase "CBD or any functional derivative thereof", according to some embodiments, refers to compounds and/or compositions that are substantially and/or essentially devoid of THC. In one embodiment, a composition comprising CBD or any functional derivative thereof, as described herein is substantially and/or essentially devoid of THC.

The phrase "CBD or any functional derivative thereof", according to some embodiments, refers to compounds and/or compositions that comprise at least 80% CBD or any functional derivative thereof. The phrase "CBD or any functional derivative thereof", according to some embodiments, refers to compounds and/or compositions that comprise at least 90% CBD or any functional derivative thereof. The phrase "CBD or any functional derivative thereof", according to some embodiments, refers to compounds and/or compositions that comprise at least 92% CBD or any functional derivative thereof. The phrase "CBD or any functional derivative thereof", according to some embodiments, refers to compounds and/or compositions that comprise at least 95% CBD or any functional derivative thereof. The phrase "CBD or any functional derivative thereof", according to some embodiments, refers to compounds and/or compositions that comprise at least 97% CBD or any functional derivative thereof. The phrase "CBD or any functional derivative thereof", according to some embodiments, refers to compounds and/or compositions that comprise at least 99% CBD or any functional derivative thereof.

In one embodiment, substantially and/or essentially devoid of THC is less than 10% by weight or weight/weight THC. In one embodiment, substantially and/or essentially devoid of THC is less than 7% by weight or weight/weight THC. In one embodiment, substantially and/or essentially devoid of THC is less than 5% by weight or weight/weight THC. In one embodiment, substantially and/or essentially devoid of THC is less than 3% by weight or weight/weight THC. In one embodiment, substantially and/or essentially devoid of THC is less than 1% by weight or weight/weight THC. In one embodiment, substantially and/or essentially devoid of THC is less than 0.5% by weight or weight/weight THC. In one embodiment, substantially and/or essentially devoid of THC is less than 0.3% by weight or weight/weight THC. In one embodiment, substantially and/or essentially devoid of THC is less than 0.1% by weight or weight/weight THC.

*Cannabis sativa*, also termed marijuana, produces a variety of Cannabinoids, including $\Delta^9$-tetrahydrocannabinol (THC) and Cannabidiol (CBD). The term "cannabinoids" refers to a heterogeneous family of molecules usually exhibiting pharmacological properties by interacting with specific receptors. To date, two membrane receptors for cannabinoids, both coupled to G protein and named CB1 and CB2 have been identified. While CB1 receptors are mainly expressed in the central and peripheral nervous system, CB2 receptors have been reported to be more abundantly detected in cells of the immune system.

THC is the main psychoactive Cannabinoid in *Cannabis*, and while it is used as a treatment for a number of medical conditions, its use is strongly limited by the unavoidable psychotropic effects.

In the methods described herein, cannabidiol, or a functional variant thereof, is administered to a subject suffering from severe forms of acute and/or chronic GVHD. In the methods described herein, cannabidiol, or a functional variant thereof, free or substantially free of THC, is administered to a subject suffering from severe forms of acute and/or chronic GVHD. In the methods described herein, purified or substantially purified (greater than 80% w/w, 85% w/w, 90%, w/w 95% w/w or 97% w/w) cannabidiol, or a functional variant thereof, is administered to a subject suffering from acute and/or chronic GVHD. Cannabidiol constitutes up to 40% of *Cannabis sativa* extracts, and is recognized as a major non-psychoactive cannabinoid, with a remarkable lack of any cognitive and psychoactive actions. CBD, also termed 2-[(6R)-3-Methyl-6-prop-1-en-2-yl-1cyclohex-2-envyl]-5pentylbenzene-1,3-diol, has the molecular formula of $C_{21}H_{30}O_2$. The chemical structure of CBD is shown in Formula I:

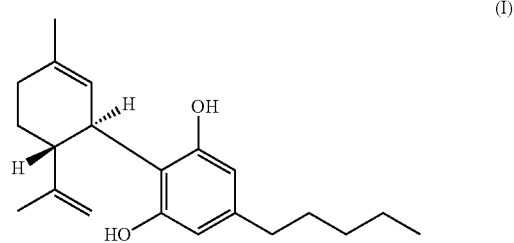 [SMILES: C=C(C)[C@@H]1CCC(C)=C[C@H]1c1c(O)cc(CCCCC)cc1O]

(I)

Cannabidiol is insoluble in water but soluble in organic solvents, such as oil. Accordingly, CBD can be formulated for use in the described methods through use of any organic solvent known to the pharmaceutical arts, including, but not limited to edible oils. When formulated for oral administration, any edible oil can be used in the CBD formulation, including olive oil.

A CBD derivative, is in some embodiments, a metabolite of CBD such as but not limited to: (−)-7-hydroxy-CBD and (−)-CBD-7-oic acid and their dimethylheptyl (DMH) homologs, as well as of the corresponding compounds in the enantiomeric (+)-CBD series. A CBD derivative is characterized, in some embodiments, by a structure wherein at least one of the hydroxyl substituent groups is converted to a stable form thereof. In one embodiment, a CBD derivative is cannabinol comprising a quinone ring. In one embodiment, a CBD derivative is an endocannabinoid derivative. In some embodiments, a CBD derivative is described in Frank D King; G Lawton; A W Oxford Progress in medicinal chemistry. Vol. 44. Pages 207-331, Elsevier Science, 2006 ISBN: 0080462103 9780080462103 which is hereby incorporated by reference in its entirety.

The safety of Cannbidiol has been shown in several clinical studies performed in patient suffering from psychological or neurological disorders. The reports indicate that administration of Cannbidiol in doses of up to 1500 mg per day resulted without any significant adverse effects. In some embodiment, the dose, dosage, or daily dose or daily dosage of Cannbidiol or a functional derivative thereof is 50 to 2500 mg. In some embodiment, the dose, dosage, or daily dose or daily dosage of Cannbidiol or a functional derivative thereof is 150 to 1500 mg. In some embodiment, the dose, dosage, or daily dose or daily dosage of Cannbidiol or a functional derivative thereof is 100 to 1000 mg. In some embodiment, the dose, dosage, or daily dose or dosage of Cannbidiol or a functional derivative thereof is 200 to 1000 mg. In some embodiment, the dose, dosage, or daily dose or daily dosage of Cannbidiol or a functional derivative thereof is the therapeutically effective dose.

The methods of the present invention provide long desired therapy of acute and chronic GVHD by inhibiting the destructive immunologic process, alleviate symptoms associated with GVHD and/or steroidal therapy, and prevent disease progression. Principal components of GVHD therapy, according to this invention, may include systemic treatment with immunosuppressive drugs or immune modulators integrated with ancillary therapy (non-systemic treatment directed to control the symptoms such as topical corticosteroids, and cyclosporine eye drops) and supportive care (interventions that are directed at control of organ-specific or systemic symptoms such as antibiotics for prevention of infections and physical therapy) and a therapeutic composition comprising Cannbidiol or a functional derivative thereof. The methods for treating acute and chronic GVHD of the present invention provide, in some embodiments, treatment with Cannbidiol or a functional derivative thereof combined with systemic treatment of prednisone, optionally combined with cyclosporine and/or tacrolimus. In some embodiments, Cannbidiol or a functional derivative thereof inhibit and/or decrease side-effects of a steroid, prednisone, tacrolimus, cyclosporine, or any combination thereof.

In some embodiments, CBD as described herein alleviates symptoms associated with both acute and chronic GVHD in transplanted patients.

The present invention now demonstrates the beneficial effects of treatment with Cannbidiol or a functional derivative thereof for the prevention or treatment of acute and chronic GVHD in transplanted patients. More specifically, the present invention demonstrates that treatment with the Cannabidiol or a functional derivative thereof compositions of the invention significantly reduces the incidence of acute and chronic GVHD and its severity, as well as other complications associated with the disease such as infections.

In some embodiments, the methods described herein are for treatment of acute GVHD, such as severe acute GVHD, for example Grade III or Grade IV GVHD. The acute GVHD for treatment by the described methods is in some embodiments be refractory to the currently-used therapies such as but not limited to: steroidal GVHD therapy. In other embodiments, CBD-inclusive treatments replace or accompany currently-used first-line acute GVHD treatments.

In one embodiment, provided a method for treating a subject afflicted with acute graft versus host disease (GVHD) or chronic GVHD comprising administering to the subject a therapeutically effective amount of a composition comprising a cannabidiol (CBD) or a functional derivative thereof, thereby treating a subject afflicted with acute graft versus host disease (GVHD) or chronic GVHD.

In one embodiment, GVHD is a steroid-refractory GVHD. In one embodiment, steroid-refractory GVHD is defined in: H. Joachim Deeg. How I treat refractory acute GVHD. Blood. 2007 May 15; 109(10): 4119-412 (PMCID: PMC1885485), S. Arai, J. Margolis, M. Zahurak, V. Anders, and G. B. Vogelsang, "Poor outcome in steroid-refractory graft-versus-host disease with antithymocyte globulin treatment," Biology of Blood and Marrow Transplantation, vol. 8, no. 3, pp. 155-160, 2002, Jason R. Westin, Rima M. Saliba, Marcos De Lima, Amin Alousi, Chitra Hosing, Muzaffar H. Qazilbash, I Issa F. Khouri, Elizabeth J. Shpall, Paolo Anderlini, Gabriela Rondon, Borje S. Andersson, Richard Champlin, and Daniel R. Couriel. Steroid-Refractory Acute GVHD: Predictors and Outcomes. Advances in Hematology. Volume 2011 (2011) pages 1-8, Article ID 601953, all of which are incorporated by reference in their entirety.

In one embodiment, acute GVHD is steroid-refractory GVHD. In one embodiment, acute GVHD is steroid-refractory GVHD. In one embodiment, a subject suffering from steroid-refractory GVHD will not respond (GVHD and associated side effects are not inhibited and/or treated) to methylprednisolone (MP), 0.5 to 20 mg/kg per day for 2 to 30 days. In one embodiment, a subject suffering from steroid-refractory GVHD will not respond (GVHD and associated side effects are not inhibited and/or treated) to MP, 2 to 15 mg/kg per day for 2 to 30 days. In one embodiment, a subject suffering from steroid-refractory GVHD will not respond (GVHD and associated side effects are not inhibited and/or treated) to methylprednisolone (MP), 2 to 12 mg/kg per day for 2 to 30 days.

In one embodiment, 2 to 30 days is 2 to 5 days. In one embodiment, 2 to 30 days is 2 to 5 days. In one embodiment, 2 to 30 days is 3 to 15 days. In one embodiment, 2 to 30 days is 3 to 6 days. In one embodiment, 2 to 30 days is 3 to 14 days. In one embodiment, 2 to 30 days is 10 to 30 days. In one embodiment, 2 to 30 days is 12 to 25 days. In one embodiment, 2 to 30 days is 3 to 25 days.

In one embodiment, a subject suffering from steroid-refractory GVHD will not respond (GVHD and associated side effects are not inhibited and/or treated) to a steroid treatment of 0.5 to 25 mg/kg per day for 2 to 30 days. In one embodiment, a subject suffering from steroid-refractory GVHD will not respond (GVHD and associated side effects are not inhibited and/or treated) to a combined steroid treatment of 0.5 to 25 mg/kg per day for 2 to 30 days. In one embodiment, treatment of GVHD includes inhibiting the progression from grade IIa to grade IIb and/or from grade IIb to grade III and/or from grade III to grade IV. In one embodiment, steroid-refractory GVHD may be characterized as GVHD wherein steroid treatment fails to inhibit the progression from grade IIa to grade IIb and/or from grade IIb to grade III and/or from grade III to grade IV. In one embodiment, treatment of GVHD includes inhibiting the progression from grade IIa, grade IIb and/or grade III to grade IV. In one embodiment, treatment of GVHD includes inhibiting the progression from grade IIa to grade III. In one embodiment, treatment of GVHD includes inhibiting the progression from a grade lower than IV to grade IV.

In one embodiment, a steroid is a corticosteroid and/or glucocorticoid or a combination of glucocorticoids and/or corticosteroids. In one embodiment, the steroid is methylprednisolone, prednisolone, hydrocortisone, dexamethasone, beclomethasone, budesonide, clobetasol, triamcinolone, fluticasone, mometasone, Diflorasone Desoximetasone, aclometasone, fluocinonide, halobetasol, flurandrenolide, betamethasone, cortisone, prednisone or any equivalents thereof and/or a combination thereof.

In one embodiment, steroid daily dose is a single dose per day. In one embodiment, steroid daily dose is divided to 2 to 8 portions/doses per day. In one embodiment, steroid treatment includes 0.2 to 25 mg/kg (body weight) per day steroid, for 2 to 30 days.

In one embodiment, a subject as described herein is a human. In one embodiment, a subject as described cannot benefit from steroid treatment. In one embodiment, a steroid treatment is refractory to a subject such as described herein.

Treating, according to some embodiments, includes inhibiting the progression or deterioration of GVHD. In one embodiment, inhibiting the progression of GVHD is inhibiting the progression from grade II to grade III GVHD. In one embodiment, inhibiting the progression of GVHD is inhibiting the progression from grade III to grade IV GVHD. In one embodiment, inhibiting the progression of GVHD is reducing the risk of death in grade III and grade IV GVHD patients. In another embodiment, grade III and grade IV GVHD are defined as acute GVHD. In another embodiment, acute GVHD is a deteriorating or progressing GVHD.

In one embodiment, a therapeutically effective amount of a composition comprising a CBD or a functional derivative thereof comprises 0.5 mg to 1 g of a CBD or a functional derivative thereof. In one embodiment, a therapeutically effective daily dose of a CBD or a functional derivative thereof comprises 0.5 mg to 1 g of a CBD or a functional derivative thereof. In one embodiment, a therapeutically effective amount of a composition comprising a CBD or a functional derivative thereof comprises 5 mg to 750 mg of a CBD or a functional derivative thereof. In one embodiment, a therapeutically effective daily dose of a CBD or a functional derivative thereof comprises 5 mg to 750 mg of a CBD or a functional derivative thereof. In one embodiment, a therapeutically effective amount of a composition comprising a CBD or a functional derivative thereof comprises 5 mg to 600 mg of a CBD or a functional derivative thereof. In one embodiment, a therapeutically effective daily dose of a CBD or a functional derivative thereof comprises 5 mg to 600 mg of a CBD or a functional derivative thereof. In one embodiment, a therapeutically effective amount of a composition comprising a CBD or a functional derivative thereof comprises 50 mg to 500 mg of a CBD or a functional derivative thereof. In one embodiment, a therapeutically effective daily dose of a CBD or a functional derivative thereof comprises 50 mg to 500 mg of a CBD or a functional derivative thereof. In one embodiment, a therapeutically effective amount of a composition comprising a CBD or a functional derivative thereof comprises 80 mg to 400 mg of a CBD or a functional derivative thereof. In one embodiment, a therapeutically effective daily dose of a CBD or a functional derivative thereof comprises 80 mg to 400 mg of a CBD or a functional derivative thereof. In one embodiment, a therapeutically effective daily dose of a CBD or a functional derivative thereof comprises 80 mg to 600 mg of a CBD or a functional derivative thereof. In one embodiment, a single therapeutically effective dosage of CBD or a functional derivative thereof comprises 30 mg to 400 mg of a CBD or a functional derivative thereof. In one embodiment, a single therapeutically effective dosage of CBD or a functional derivative thereof comprises 50 mg to 500 mg of a CBD or a functional derivative thereof. In one embodiment, a single therapeutically effective dosage of CBD or a functional derivative thereof comprises 80 mg to 300 mg of a CBD or a functional derivative thereof. In one embodiment, a single therapeutically effective dosage of CBD or a functional derivative thereof comprises 100 mg to 200 mg of a CBD or a functional derivative thereof.

In one embodiment, a composition as described herein is a topical composition. In one embodiment, a composition as described herein is an oral composition. In one embodiment, a composition as described herein is a systemic composition. In one embodiment, a subject as described herein is treated with a combination of steroid compositions selected from: a topical composition, a systemic composition, and an oral composition.

In one embodiment, the method further includes administering at least one additional GVHD therapeutic agent. In one embodiment, an additional GVHD therapeutic agent is: Antithymocyte globulin, Alemtuzumab, an Interleukin-2 receptor antagonist, a steroid, an antitumour necrosis factor antibody, Mycophenolate mofetil, Sirolimus, Pentostatin, Mesenchymal stem cells, or any combination thereof. In some embodiments, a subject as described herein is treated with a steroid prior to the treatment with a CBD or a functional derivative thereof as described herein. In some embodiments, a subject as described herein is treated with CBD or a functional derivative thereof and a steroid. In some embodiments, a subject as described herein is treated with CBD or a functional derivative thereof and at least one additional GVHD therapeutic agent.

Conditions Associated with GVHD

In one embodiment, the invention provides a method for treating a subject afflicted with a condition associated with acute graft versus host disease (GVHD) or chronic GVHD, comprising administering to the subject a therapeutically effective amount of a composition comprising a cannabidiol (CBD) or a functional derivative thereof, thereby treating a subject afflicted with a condition associated with acute graft versus host disease (GVHD).

In one embodiment, a condition associated with acute graft versus host disease (GVHD) or chronic GVHD is selected from the group consisting of: maculopapular rash, generalized erythroderma and bullous formation, hyperbilirubinemia, diarrhea, nausea, scleroderma, or any combination thereof. In one embodiment, a condition associated with acute graft versus host disease (GVHD) or chronic GVHD comprises a side effect resulting from a steroid treatment. In one embodiment, a condition associated with acute graft versus host disease (GVHD) or chronic GVHD comprises cholestatic hyperbilirubinemia. In one embodiment, a condition associated with acute graft versus host disease (GVHD) or chronic GVHD comprises cholestatic hyperbilirubinemia. In one embodiment, provided herein a method for treating a subject afflicted with GVHD and hyperbilirubinemia. In one embodiment, provided herein a method for reducing bilirubin blood level in a subject afflicted with GVHD and hyperbilirubinemia. In one embodiment, provided herein a method for reducing bilirubin blood level by at least 10% in a subject afflicted with GVHD and hyperbilirubinemia. In one embodiment, provided herein a method for reducing bilirubin blood level by at least 20% in a subject afflicted with GVHD and hyperbilirubinemia. In one embodiment, provided herein a method for reducing bilirubin blood level by at least 30% in a subject afflicted with GVHD and hyperbilirubinemia. In one embodiment, provided herein a method for reducing bilirubin blood level by at least 40% in a subject afflicted with GVHD and hyperbilirubinemia. In one embodiment, provided herein a method for reducing bilirubin blood level by at least 50% in a subject afflicted with GVHD and hyperbilirubinemia. In one embodiment, provided herein a method for reducing bilirubin blood level by at least 60% in a subject afflicted with GVHD and hyperbilirubinemia.

In one embodiment, treating a subject afflicted with a condition associated with acute graft versus host disease (GVHD) or chronic GVHD is reducing the severity of a condition associated with acute graft versus host disease (GVHD) or chronic GVHD. In one embodiment, treating a subject afflicted with a condition associated with acute graft versus host disease (GVHD) or chronic GVHD is inhibiting and/or ameliorating a condition associated with acute graft versus host disease (GVHD) or chronic GVHD.

In one embodiment, acute GVHD is acute skin GVHD grade III or grade IV. In one embodiment, acute GVHD is acute liver GVHD grade III or grade IV. In one embodiment, acute GVHD is acute gastrointestinal GVHD grade III or grade IV. In one embodiment, acute liver GVHD grade III or grade IV includes hyperbilirubinemia.

In one embodiment, provided a method for enhancing the therapeutic effect of a steroid in a subject in need of a steroid therapy, comprising administering to the subject the steroid and a cannabidiol (CBD) or a functional derivative thereof, thereby enhancing the therapeutic effect of a steroid in a subject in need of a steroid therapy. In one embodiment, provided a method for enhancing the therapeutic effect of a steroid dose or dosage in a subject in need of a steroid therapy, comprising administering to the subject the steroid dose or dosage and a cannabidiol (CBD) or a functional derivative thereof, thereby enhancing the therapeutic effect of a steroid dose or dosage in a subject in need of a steroid therapy. In one embodiment, enhancing the therapeutic effect of a steroid is maintaining a fixed dose and combining it with a cannabidiol (CBD) or a functional derivative thereof. In one embodiment, enhancing the therapeutic effect of a steroid is rendering a refractory steroid dose and/or dosage, therapeutically effective. In one embodiment, enhancing the therapeutic effect of a steroid is rendering a sub-efficient steroid dose and/or dosage, therapeutically effective. In one embodiment, enhancing the therapeutic effect of a steroid is avoiding increase in steroid dose and/or dosage. In one embodiment, enhancing the therapeutic effect of a steroid is avoiding increase in steroid dose and/or dosage due to insufficient and/or poor clinical effect. In one embodiment, enhancing the therapeutic effect of a steroid is reducing the duration of steroid treatment. In one embodiment, a steroid is glucocorticosteroid, corticosteroid or any steroid known to one of skill in the art or described herein.

In one embodiment, provided a pharmaceutical composition comprising a cannabidiol (CBD) or a functional derivative thereof for use in enhancing the therapeutic effect of a steroid. In one embodiment, provided a pharmaceutical composition comprising a cannabidiol (CBD) or a functional derivative thereof for use in reducing a dose or a dosage of a steroid. In one embodiment, provided a pharmaceutical composition comprising a cannabidiol (CBD) or a functional derivative thereof for use in reducing a dose or a dosage of a steroid while maintaining or enhancing the steroid's therapeutic effect. In one embodiment, provided a pharmaceutical composition comprising a cannabidiol (CBD) or a functional derivative thereof for use in maintaining or enhancing the therapeutic effect of a steroid therapy. In one embodiment, maintaining or enhancing the therapeutic effect of a steroid therapy, according to the methods of the invention, include reducing the dosage or dose of a steroid in a subject treated with a cannabidiol (CBD) or a functional derivative thereof.

In one embodiment, provided a pharmaceutical composition comprising a cannabidiol (CBD) or a functional derivative thereof for reducing the effective dose of a steroid. In one embodiment, provided a pharmaceutical composition comprising a cannabidiol (CBD) or a functional derivative thereof for reducing a side effect associated with steroid treatment. In one embodiment, provided a pharmaceutical composition comprising a cannabidiol (CBD) or a functional derivative thereof for reducing the effective dose of a steroid and thereby reducing a side effect associated with steroid treatment.

In one embodiment, provided a pharmaceutical composition comprising a cannabidiol (CBD) or a functional derivative thereof for reducing the effective dose of a steroid. In one embodiment, "effective dose" is the "therapeutically effective dose". In one embodiment, a pharmaceutical composition comprising a cannabidiol (CBD) or a functional derivative thereof reduces the effective dose of steroid by at least 20% w/w. In one embodiment, a pharmaceutical composition comprising a cannabidiol (CBD) or a functional derivative thereof reduces the effective dose of steroid by 10% to 70% w/w. In one embodiment, a pharmaceutical composition comprising a cannabidiol (CBD) or a functional derivative thereof reduces the effective dose of steroid by at least 30% w/w. In one embodiment, a pharmaceutical composition comprising a cannabidiol (CBD) or a functional derivative thereof reduces the effective dose of steroid by at least 40% w/w. In one embodiment, a pharmaceutical composition comprising a cannabidiol (CBD) or a functional derivative thereof reduces the effective dose of steroid by at least 50% w/w. In one embodiment, a pharmaceutical composition comprising a cannabidiol (CBD) or a functional derivative thereof reduces the effective dose of steroid by at least 60% w/w.

In one embodiment, provided a method for enhancing the therapeutic effect of a steroid in a subject afflicted with graft versus host disease (GVHD), comprising administering to the subject the steroid and a cannabidiol (CBD) or a functional derivative thereof, thereby enhancing the therapeutic effect of a steroid in a subject afflicted with graft versus host disease (GVHD). In one embodiment, GVHD is chronic GVHD. In one embodiment, GVHD is acute GVHD.

In one embodiment, provided a method for reducing a side effect associated with a steroid in a subject afflicted with graft versus host disease (GVHD) and treated with a steroid, comprising administering to the subject the steroid and a cannabidiol (CBD) or a functional derivative thereof. In one embodiment, provided a method for reducing a side effect associated with a steroid in a subject afflicted with graft versus host disease (GVHD) and treated with a steroid, comprising administering to the subject the steroid and a cannabidiol (CBD) or a functional derivative thereof. In one embodiment, provided a method for reducing the effective dose of a steroid in a subject afflicted with graft versus host disease (GVHD) and treated with a steroid, comprising administering to the subject a reduced steroid dose and a cannabidiol (CBD) or a functional derivative thereof.

In one embodiment, a steroid is an anabolic steroids. In one embodiment, a steroid is a corticosteroid. In one embodiment, a subject in need of a steroid therapy is afflicted with inflammation. In one embodiment, a subject in need of a steroid therapy is in need of reducing and/or inhibiting an immune response.

In some embodiments, a reduced dose includes at least 15% (by weight) less steroid. In some embodiments, a reduced dose includes at least 20% (by weight) less steroid. In some embodiments, a reduced dose includes at least 25% (by weight) less steroid. In some embodiments, a reduced dose includes at least 30% (by weight) less steroid. In some embodiments, a reduced dose includes at least 40% (by weight) less steroid. In some embodiments, a reduced dose includes at least 50% (by weight) less steroid.

In some embodiments, the phrase "effective dose" is the dose effective for treating or ameliorating GVHD as described herein. In some embodiments, the phrase "effective dose" is synonymous with the phrase "daily effective dose" as described herein. In some embodiments, the phrase "effective dose" is the dose effective for reducing bilirubin level in the blood of a subject afflicted with acute liver GVHD. In some embodiments, the phrase "effective dose" is the dose effective for reducing and/or inhibiting a pathology and/or risk associated with chronic or acute GVHD. In some embodiments, reducing the effective dose of a steroid results in minimizing or reducing at least one side effect associated with steroid treatment.

In one embodiment, provided a method for enhancing the therapeutic GVHD effect of a given steroid dose in a subject afflicted with graft versus host disease (GVHD) and treated with a steroid, comprising administering to the subject the given steroid dose and a cannabidiol (CBD) or a functional derivative thereof.

In some embodiments, enhancing the therapeutic effect of a steroid enables the reduction of dosing. In some embodiments, enhancing the therapeutic effect of a steroid is rendering a refractory steroid dose a therapeutic effective dose. In some embodiments, a refractory steroid dose is any steroid dose found to be refractory in a subject afflicted with GVHD. In one embodiment, a refractory steroid dose is a daily steroid dose of 0.2 to 20 mg/kg (body weight) per day found to be refractory in terms of therapeutic effect in a subject afflicted with GVHD. In one embodiment, provided a method for treating a subject afflicted with steroid-refractory GVHD, comprising administering to the subject: (a) a steroid; and (b) a cannabidiol (CBD) or a functional derivative thereof. In some embodiments, enhancing the therapeutic effect of a steroid is enhancing the therapeutic effect of a given or a fixed dose of a steroid. In some embodiments, enhancing the therapeutic effect of a steroid is enhancing steroid therapy which is reducing or gradually reducing (within a period of 3 days to 6 months) the administered dosage or dose of a steroid while maintain and/or improving/enhancing/maintaining: (a) the therapeutic effect of the reduced dose of a steroid; or (b) the efficacy of the steroid therapy. In some embodiments, enhancing the therapeutic effect of a steroid is rendering a refractory steroid therapy (treatment with a given steroid dose)—therapeutically effec-tive and optionally further reducing or gradually reducing (within a period of 3 days to 6 months) the administered dosage or dose of a steroid (the dose or dosage found previously to be refractory) while continuously maintaining and/or improving/enhancing: (a) the therapeutic effect of the reduced dose of a steroid; or (b) the efficacy of the steroid therapy.

In one embodiment, the steroid is Methyprednisolone or prednisone and both the refractory steroid dose the therapeutic effective dose is 0.1 to 3 mg/kg/day. In one embodiment, the steroid is Methyprednisolone or prednisone and both the refractory steroid dose the therapeutic effective dose is 0.2 to 2 mg/kg/day. In one embodiment, the steroid is Methyprednisolone or prednisone and both the refractory steroid dose the therapeutic effective dose is 0.5 to 1.8 mg/kg/day.

In some embodiments, enhancing the therapeutic effect of a given dose of a steroid or reducing the given dose of a steroid by maintain or improving the steroid's therapeutic effect can be a process wherein the steroid dose administered with CBD is gradually decreased over time. In some embodiments, enhancing the therapeutic effect of a given dose of a steroid or reducing the given dose of a steroid by maintain or improving the steroid's therapeutic effect can be a process wherein the steroid dose administered with CBD is gradually decreased over a period of 3 days to 6 months. In some embodiments, enhancing the therapeutic effect of a given dose of a steroid or reducing the given dose of a steroid by maintain or improving the steroid's therapeutic effect can be a process wherein the steroid dose administered with CBD is gradually decreased over a period of 3 weeks to 3 months. over a period of 3 weeks to 2 months.

In other embodiments, the methods include treatment of the conditions associated with severe acute GVHD, including pathologies of the skin, liver, and gastrointestinal tract. Such conditions or symptoms include maculopapular rash, generalized erythroderma and bullous formation, greater than normal levels of bilirubin (cholestatic hyperbilirubinemia; for example, greater than 2 mg %), diarrhea, and nausea.

In still other embodiments, the described methods include treatment of severe chronic forms of GVHD, including, severe classing and overlap forms of chronic GVHD.

In some embodiments, the treatment of the severe chronic GVHD is treatment of one or more symptoms or conditions associated with chronic GVHD. In one embodiment, conditions associated with the chronic GVHD are known to one of skill in the art.

In other embodiments treatment with the Cannabidiol or a functional derivative thereof compositions of the invention treats GVHD associated symptoms and signs of the various organs and systems, including the skin, nails, mouth, eyes, female genitalia, gastrointestinal tract, liver, lungs, muscles, fascia and joints.

Thus, in one aspect, the invention relates to a method of preventing, treating, ameliorating or curing acute and chronic GVHD, including Grade III or Grade IV acute GVHD, moderate to severe chronic GVHD, and steroid-refractory forms of the diseases. The method of the invention comprises the step of administering to a subject in need thereof a therapeutically effective amount of Cannabidiol or any functional derivative thereof or any pharmaceutical composition comprising the same.

In some embodiments, the Cannabidiol or any functional derivative thereof according to the present invention is a natural product extracted and/or purified from *Cannabis sativa*. In other embodiments, the CBD or functional derivative thereof is a synthetic product. In still further embodiments, the CDB-containing composition is the *Cannabis* plant itself. Whenever reference is made herein to "*Cannabis sativa*" the same applies also to other *Cannabis* plants producing Cannabidiol, including *Cannabis indica* and *Cannabis ruderalis. Cannabis sativa* is referred to herein specifically, for the sake of brevity.

In some embodiments, Cannabidiol, or any derivative thereof according to the present invention, can be administered to patients before or after any type of allogeneic hematopoietic stem cell transplantation, including but not limited to sibling and unrelated-donor bone marrow or peripheral-blood stem cell transplantation, cord blood transplantation, and haploidentical bone marrow or peripheral-blood stem cell transplantation.

In some embodiments, the CBD, or a functional derivative thereof, is administered following onset of symptoms of the acute or chronic GVHD as described herein. In other embodiments, the CBD, or a functional derivative thereof, is administered after a diagnosis is made of the form of GVHD. In other embodiments, the CBD, or a functional derivative thereof, is administered with a steroid. In other embodiments, the CBD or a functional derivative thereof, is administered before and/or after a steroid.

Administration of the Cannabidiol compositions to a patient intended to undergo transplantation may start between 14 to 5 days prior to the medical procedure, more specifically 8 days before the transplant. Alternatively, treatment with the Cannabidiol compositions may begin between 1 to 30 days after transplantation, more specifically, 1 day after the transplant.

Administration of the Cannabidiol or a functional derivative thereof compositions to a subject as described herein lasts for at least 20 days post transplantation or post development of GVHD. Administration of the Cannabidiol or a functional derivative thereof compositions to a subject as described herein lasts for at least 30 days post transplantation or post development of GVHD. Administration of the Cannabidiol or a functional derivative thereof compositions to a subject as described herein lasts for at least 20 days post transplantation or post development of GVHD. Administration of the Cannabidiol or a functional derivative thereof compositions to a subject as described herein lasts for at least 40 days post transplantation or post development of GVHD. Administration of the Cannabidiol or a functional derivative thereof compositions to a subject as described herein lasts for at least 50 days post transplantation or post development of GVHD. Administration of the Cannabidiol or a functional derivative thereof compositions to a subject as described herein lasts for at least 60 days post transplantation or post development of GVHD. Administration of the Cannabidiol or a functional derivative thereof compositions to a subject as described herein lasts for at least 70 days post transplantation or post development of GVHD. Administration of the Cannabidiol or a functional derivative thereof compositions to a subject as described herein lasts for at least 80 days post transplantation or post development of GVHD. Administration of the Cannabidiol or a functional derivative thereof compositions to a subject as described herein lasts for at least 90 days post transplantation or post development of GVHD. Administration of the Cannabidiol or a functional derivative thereof compositions to a subject as described herein lasts for at least 100 days post transplantation or post development of GVHD.

Administration of the Cannabidiol or a functional derivative thereof compositions to a subject as described herein lasts for at least 20 days from the day Cannabidiol or a functional derivative thereof was administered for the first time. Administration of the Cannabidiol or a functional derivative thereof compositions to a subject as described herein lasts for at least 30 days from the day Cannabidiol or a functional derivative thereof was administered for the first time. Administration of the Cannabidiol or a functional derivative thereof compositions to a subject as described herein lasts for at least 20 days from the day Cannabidiol or a functional derivative thereof was administered for the first time. Administration of the Cannabidiol or a functional derivative thereof compositions to a subject as described herein lasts for at least 40 days from the day Cannabidiol or a functional derivative thereof was administered for the first time. Administration of the Cannabidiol or a functional derivative thereof compositions to a subject as described herein lasts for at least 50 days from the day Cannabidiol or a functional derivative thereof was administered for the first time. Administration of the Cannabidiol or a functional derivative thereof compositions to a subject as described herein lasts for at least 60 days from the day Cannabidiol or a functional derivative thereof was administered for the first time. Administration of the Cannabidiol or a functional derivative thereof compositions to a subject as described herein lasts for at least 70 days from the day Cannabidiol or a functional derivative thereof was administered for the first time. Administration of the Cannabidiol or a functional derivative thereof compositions to a subject as described herein lasts for at least 80 days from the day Cannabidiol or a functional derivative thereof was administered for the first time. Administration of the Cannabidiol or a functional derivative thereof compositions to a subject as described herein lasts for at least 90 days from the day Cannabidiol or a functional derivative thereof was administered for the first time. Administration of the Cannabidiol or a functional derivative thereof compositions to a subject as described herein lasts for at least 100 days from the day Cannabidiol or a functional derivative thereof was administered for the first time. The first time Cannabidiol or a functional derivative was administered, in some embodiment, is the day grade IIa, grade IIb, grade III or grade IV, was diagnosed.

In some embodiments, a GVHD patient as described herein (the "subject") is pre-treated with a calcineurine inhibitor (cyclosporine or tacrolimus) with or without a steroid such as but not limited to prednisone. In some embodiments, a GVHD patient as described herein (the "subject") is treated with CBD or a functional derivative thereof with a calcineurine inhibitor (cyclosporine or tacrolimus) with or without a steroid such as but not limited to prednisone. In some embodiments, a GVHD patient as described herein (the "subject") is treated with CBD or a functional derivative thereof with fludarabine, busulfex, melphalan, ATG or any combination thereof. In some embodiments, a GVHD patient as described herein is refractory to tacrolimus, a systemic steroid, a topical steroid or any combination thereof. In some embodiments, a GVHD patient as described herein is treated with 150 to 500 mg CBD or a functional derivative thereof per day and 15 to 100 mg steroid (such as prednisone) per day.

In one embodiment, a subject is afflicted with grade 3 or 4 acute GVHD of the gastro-intestinal tract (GIT). In one embodiment, a subject is afflicted with grade 3 or 4 acute GVHD of the liver. In one embodiment, a subject is afflicted with grade 3 or 4 acute GVHD of the skin. In one embodiment, a subject is afflicted with GVHD is afflicted with an overlap syndrome (concomitant acute plus chronic GVHD features).

In some embodiments, a GVHD patient as described herein (the "subject") is treated with CBD or a functional derivative thereof with mycophenolate mofetil. In some embodiments, a GVHD patient as described herein (the "subject") is treated with CBD or a functional derivative thereof with extra-corporeal photopheresis (ECP). In some embodiments, a GVHD patient as described herein (the "subject") if further afflicted with myopathy. In some embodiments, the methods described herein lower blood bilirubin level in a subject having GVHD, from above 1.4 mg % or above 1.2 milligrams per deciliter (blood) to normal level (0.7-1.3 mg % or 1.2 milligrams per deciliter (mg/dL) blood) within a week or within 1 to 5 days. In some embodiments, the methods described herein lower blood bilirubin level in a subject having GVHD, from above 3.0 mg % or above 3.0 milligrams per deciliter (blood) to normal level (0.7-1.3 mg % or 1.2 milligrams per deciliter (mg/dL) blood) within a week or within 1 to 5 days. In some embodiments, the methods described herein lower blood bilirubin level in a subject having GVHD, from above 4.0 mg % (blood) to normal level (0.7-1.3 mg % or 12 milligrams per deciliter (mg/dL) blood) within a week or within 1 to 5 days. In some embodiments, the methods described herein lower blood bilirubin level in a subject having GVHD, from above 6.0 mg % (blood) to normal level (0.7-1.3 mg % or 1.2 milligrams per deciliter (mg/dL) blood) within a week or within 1 to 5 days. In some embodiments, the methods described herein lower blood bilirubin level in a subject having GVHD, from 2 to 9 mg % (blood) to normal level (0.7-1.3 mg % or 1.2 milligrams per deciliter (mg/dL) blood) within a week or within 1 to 5 days.

In some embodiments, the method of the invention may optionally further comprise the step of administering at least one additional therapeutic agent, including currently used drugs given to transplanted patients, whether prior to the transplant, or afterwards. These additional therapeutic agents, specifically, any immunomodulatory agent or known medicament, may be either combined with Cannabidiol or may be administered separately in an additional separate step having an optional different mode of administration.

In some embodiments, the method optionally further comprises the step of administering at least one additional therapeutic agent including but not limited to currently available medicines e.g. cyclosporine, tacrolimus, methotrexate, mycophenolate mofetil, sirolimus, ATG, imatinib or other TKIs, azathioprine, pentostatin, thalidomide, retinoids, anti-CD20, anti-CD52, ECP, corticosteroids and mesenchymal stem cells.

The pharmaceutical compositions containing Cannabidiol according to the present invention can be administered for prophylactic and/or therapeutic treatments. In therapeutic application, compositions are administered to a patient already suffering from acute or chronic GVHD in an amount sufficient to cure or at least partially arrest the condition and its complications. An amount adequate to accomplish this is defined as a "therapeutically effective dose." In prophylactic applications, compositions containing Cannabidiol are administered to a patient who is at risk of developing acute and/or chronic GVHD, i.e. a patient being before or after allogeneic transplantation. Such an amount is defined to be a "prophylactically effective dose". Amounts effective for both prophylactic and therapeutic purposes will depend upon the risk to develop GVHD, the severity of the GVHD condition and the general state of the patient, but generally range from about 0.01 to about 10 mg/Kg body weight, specifically, about 0.5 to about 10 mg/Kg of Cannabidiol per day. Single or multiple administrations on a daily schedule can be carried out with dose levels being selected by the treating physician. It should be noted that doses of Cannabidiol can be elevated every day during the treatment period according to the clinical response of the patient, provided no significant drug related side effects present.

Additionally, the administration of Cannabidiol according to the invention, or pharmaceutical compositions comprising Cannabidiol, may be periodic, for example, the periodic administration may be effected twice daily, three times daily, or at least once daily for 2 days to 180 days, more preferably 90 to 180 days after transplantation for GVHD prevention and 2 days to 12 months (or longer as needed) for the treatment of GVHD following onset of symptoms or diagnosis.

In some embodiments, CBD is provided to a patient in once, twice, thrice or more doses per day. Specific embodiments of the invention relate to the use of typically two doses per day, each containing at least 10 mg Cannabidiol, but usually not more than a daily dose of 600 mg. In one embodiment, a daily dose comprises 150 to 400 mg CBD administered in one or two dosages.

In some embodiments, an exemplary concentration of Cannabidiol in oil, e.g. olive oil, effective for the prevention and/or treatment of GVHD, such as Grade III or Grade IV acute GVHD or severe chronic GVHD, may range typically between about 1% weight/volume and about 3% weight/volume, more specifically, 2.5% weight/volume.

It should be noted that the Cannabidiol compositions according to the present invention can be prepared in any type of oil, such as canola oil, olive oil, sunflower oil, soybean oil, corn oil, or paraffin oil.

The administration of pharmaceutical compositions comprising Cannabidiol or any derivative thereof according to the invention for the prevention, treatment, amelioration of GVHD in any form, may be any one of oral, sublingual, buccal, rectal, vaginal, topical, parenteral, intravenous, intramuscular, subcutaneous, intra-peritoneal or via oral or nasal inhalation, such as in the form of purified vapors or by smoking of *Cannabis*.

Compositions and formulations for oral administration include powders or granules, suspensions or solutions in water or non-aqueous media, capsules, sachets, lozenges (including liquid-filled), chews, multi- and nano-particulates, gels, solid solution, liposome, films, ovules, sprays or tablets. Thickeners, flavoring agents, diluents, emulsifiers, dispersing aids or binders may be desirable.

Pharmaceutical compositions used to treat subjects in need thereof according to the invention, which may conveniently be presented in unit dosage form, may be prepared according to conventional techniques well known in the pharmaceutical industry. Such techniques include the step of bringing into association the active ingredients with the pharmaceutical carrier(s) or excipient(s). The compositions may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. The suspension may also contain stabilizers. The pharmaceutical compositions of the present invention also include, but are not limited to, emulsions and liposome-containing formulations.

It should be understood that in addition to the ingredients particularly mentioned above, the formulations may also include other agents conventional in the art having regard to the type of formulation in question, for example those suitable for oral administration may include flavoring agents.

Pharmaceutical formulations adapted for rectal administration may be presented as suppositories or enemas.

Pharmaceutical formulations adapted for vaginal administration may be presented as pessaries, tampons, creams, gels, pastes, foams or spray formulations.

According to certain embodiments, pharmaceutical compositions comprising Cannabidiol, or any derivative thereof according to the present invention are also useful for parenteral administration, i.e., subcutaneously (s.c.), intramuscularly (i.m.), and intravenously (i.v.). The compositions for parenteral administration commonly comprise a solution of Cannabidiol dissolved in an acceptable carrier.

In one embodiment, the compositions of the invention are suitable for oral administration. The Cannabidiol compositions can be administered from one or more times per day to one or more times per week, including once every other day. Dosing is dependent on the severity of the symptoms and on the responsiveness of the subject to the treatment. The skilled artisan will appreciate that certain factors may influence the dosage and timing required to effectively treat a subject, including but not limited to the severity of the disease, previous treatments, the general health and/or age of the subject, and other diseases present.

The present invention relates to the treatment of subjects, or patients, in need thereof. By "patient" or "subject in need" it is meant any mammal for which administration of the composition of the invention is desired, in order to prevent, overcome or slow down a medical condition. As described herein, the medical condition for treatment includes Grade III or Grade IV acute GVHD, severe chronic GVHD, refractory forms of either acute or GVHD, or any of the conditions described herein that are associated with acute or GVHD (e.g. pathologies of the skin, liver, lungs, and the like).

The terms "treatment", "prevention" and "prophylaxis" refer to the complete range of therapeutically positive effects of administrating to a subject including inhibition, reduction of, alleviation of, and relief from, GVHD, specifically, acute and chronic GVHD. More specifically, treatment or prevention includes the prevention or postponement of development of the disease, prevention or postponement of development of symptoms and/or a reduction in the severity of such symptoms that will or are expected to develop. These further include ameliorating existing symptoms, preventing additional symptoms and ameliorating or preventing the underlying causes of symptoms.

It should be noted that particularly in case of human subjects, administration of the compositions of the invention to the patient includes both self-administration and administration to the patient by another person.

To provide a "preventive treatment" or "prophylactic treatment" is acting in a protective manner, to defend against or prevent something, especially a condition or disease.

As used herein, "disease", "disorder", "condition" and the like, as they relate to a subject's health, are used interchangeably and have meanings ascribed to each and all of such terms.

The term "pharmaceutical composition" refers to an active compound in any form suitable for effective administration to a subject, e.g., a mixture of the compound and at least one pharmaceutically acceptable carrier.

The term "therapeutically effective amount" is intended to mean that amount of a drug or pharmaceutical agent that will elicit the biological or medical response of a tissue or human that is being sought by a researcher, medical doctor, or other clinician, or by the subject himself.

As used herein, a "pharmaceutically acceptable carrier" means a carrier or diluent that does not cause significant irritation to a subject and does not abrogate the biological activity and properties of the administered compound.

A "pharmaceutically acceptable excipient" means an inert substance added to a pharmaceutical composition to further facilitate administration of the compound. Examples, without limitation, of excipients include calcium carbonate, calcium phosphate, various sugars and types of starch, cellulose derivatives, gelatin, vegetable oils and polyethylene glycols.

The following examples, which further describe the invention, are offered by way of illustration and are not intended to limit the invention in any manner.

EXAMPLES

Example 1: Prevention of Acute and Chronic GVHD in Allogeneic Stem Cell Transplanted Patients Forty six (46) patients over 18 years of age undergoing allogeneic hematopoietic stem cell transplantation at the Rabin Medical Center in Israel were recruited. Patients having history of psychosis or asthma, or consuming *Cannabis* during the last two months before transplantation were excluded from the study.

All patients received standard GVHD prophylaxis consisting of cyclosporine twice a day starting on day −1 with target trough levels ≥200 ng/mL in combination with short course of methotrexate (15 mg/sqm on day +1 and 10 mg/sqm on days +3 and +6). Most patients transplanted from unrelated donors received anti-T-cell globulin (ATG Fresenius) at a low dose of 5 mg/kg on days −3 to −1.

The investigational agent, CBD (STI Pharmaceuticals, Brentwood, Essex, UK) was dissolved in olive oil at a concentration of 2.5% and was orally administered from day −7 through day +30. The starting dose of CBD was 10 mg twice a day, and doses were doubled every other day to a maximal dose of 150 mg twice a day.

To estimate the prophylactic and therapeutic effect of Cannabidiol, the patients were carefully monitored and documented for the presentation of acute and chronic GVHD symptoms, the time of onset, the severity of the symptoms, the responsiveness to treatment, and the occurrence of infections.

Furthermore, a panel of 4 serum cytokines (soluble TNF receptor 1 (sTNFRI), soluble IL-2 receptor alpha (sIL2R-alpha), hepatocyte growth factor (HGF), and IL8)) were monitored. Blood samples were taken at days −7(A), 0(B), +14(C), and +28(D). The difference in blood levels between the various time points (B-A, C-B and D-C) were assessed.

Primary end points were safety and cumulative incidence of grade 2-4 and grade 3-4 GVHD by day +100. The secondary end points were cumulative incidence of chronic and severe chronic GVHD, non-relapse mortality (NRM), relapse incidence (RI), and overall survival (OS). NRM mortality was defined as death while the patient was in CR. Cumulative incidence curves were used for acute GVHD and chronic GVHD estimation, taking into account relapse and death as competing risks. Cumulative incidence curves were used for RI and NRM taking into account disease recurrence and death as competing events. Probabilities of OS and LFS were calculated using the Kaplan-Meier estimates.

Median age was 56 (range, 22 to 73) years. Most patients (n=38, 79%) had acute leukemia and 13 patients (27%) had chemo-refractory disease at transplantation. Twenty patients (42%) received allografts from unrelated donors. Thirty five patients (73%) received myeloablative conditioning. Median follow-up of survivors was 10 (range, 1.3 to 18) months. Drug compliance was good, with 32 patients (70%) taking 100% of the doses. Non compliance with study medication was mainly due to mucositis and nausea. Median dose dense among non-compliant patients was 86% (range, 43%-96%). No grade 3 to 4 toxicities related to CBD were observed.

Six patients developed grade 2 to 4 acute GVHD. Two patients had a gut-only involvement, 3 patients had involvement of skin and gut, and 1 patient had involvement of gut and liver. Median time to onset of grade 2 to 4 acute GVHD was 60 days (range, 41 to 150 days). Cumulative incidence rates of grade 2 to 4 acute GVHD at day 100 was 12.4%. Cumulative incidence rates of grade 3 to 4 acute GVHD at day 100 was 5%.

Among patients surviving more than 100 days after HCT (n=33), chronic GVHD occurred in 11 patients (overlap, n=3 and classic, n=8), with a median time to onset of 159 (range, 125 to 335) days. Of the 11 patients, 8 had limited chronic GVHD with a low stage involvement of the oral mucosa and a mild elevation of liver enzymes. In the 3 patients with severe chronic GVHD, organ involvement included eyes (n=3), mouth (n=3), skin (n=3), lungs (n=2) and musculo-skeletal (n=1). Cumulative incidence rates of overall and extensive chronic GVHD at 1 year were 43% and 19%, respectively.

Cumulative incidences of relapse at 100 days, 6 months and 12 months after HCT were 12%, 22%, and 31%, respectively. Non-relapse mortality at 100 days, 6 months and 12 months after HCT were 8.1%, 11.6%, and 11.6%, respectively. Overall survival rates at 100 days, 6 months and 12 months after HCT were 84%, 76% and 70%, respectively.

Interestingly, patients with increased D-C serum levels of IL8 and sIL2R-alpha had a relative risk of 3.8 (95% CI 0.8-17.1, p=0.1) and 2.8 (95% CI 1.1-7.5, p=0.05), respectively, for developing chronic GVHD.

The results obtained clearly indicate that administration of Cannabidiol reduces the incidence and severity of acute and chronic GVHD after allogeneic stem cell transplantation. The findings presented herein demonstrate the advantages concurrent with low toxicity and lack of psychotropic effects of Cannabidiol in preventing acute and chronic GVHD.

Example 2: CBD Treatment for Chronic GVHD

Twelve patients over 18 years of age with extensive chronic GVHD after allogeneic HCT were recruited at the Rabin Medical Center in Israel. Patients having a history of psychosis or asthma, or consuming *Cannabis* during the last two months before transplantation were excluded from the study.

Patients were presently treated with a calcineurine inhibitor (cyclosporine or tacrolimus) with or without oral prednisone.

Patients were given oral CBD 50 mg twice a day.

A clinical improvement was documented in 6 out of 8 patients with skin involvement, 2 out of 3 with lung involvement, 3 out 4 with liver involvement and 3 out of 3 with oral involvement.

The results obtained clearly indicate that administration of CBD reduces the severity of chronic GVHD.

Example 3: Cannabidiol (CBD) for Treatment of Severe (Grade 3-4) and/or Refractory Acute GVHD This example describes cases studies that show the surprising efficacy of CBD treatment of patients experiencing severe acute GVHD.

A 45 year old male with acute myeloid leukemia in second complete remission, underwent an allogeneic hematopoietic cell transplantation from a matched sibling female donor with a myeloablative conditioning consisting of fludarabine (160 mg/m$^2$) and busulfex (12.8 mg/kg). One month post-transplantation he developed classic grade 4 acute GVHD of the gastro-intestinal tract (GIT) confirmed by intestinal biopsy. He was refractory to cyclosporine and high-dose steroids, and was then given second line therapy consisting of mycophenolate mofetil followed by extra-corporeal photopheresis (ECP), from which a partial response was obtained. The patient then developed severe myopathy and became bed restricted. During tapering off of steroids he had relapse of grade 4 acute GVHD with GIT and skin involvement. He was refractory to high-dose steroids and thus started oral cannabidiol (CBD) 150 mg twice a day. After 14 days of CBD he had complete cessation of diarrhea and resolution of his skin rash. CBD was stopped several weeks later upon remission. Eighteen months following cessation of treatment, the patient has no symptoms or signs of acute GVHD. Nevertheless, he developed chronic GVHD for which he was given low dose cyclosporine and low dose prednisone.

A 31 year old male with Philadelphia positive acute lymphoid leukemia in first complete remission underwent an allogeneic hematopoietic cell transplantation from a male matched unrelated donor with reduced intensity conditioning consisting of fludarabine (150 mg/m$^2$), busulfex (12.8 mg/kg) and ATG (Fresenius, 15 mg/kg). Two months after transplantation, he developed generalized erythroderma ranked as stage 3 and grade 2 acute GVHD of the skin, which was confirmed by skin biopsy. Due to refractoriness to tacrolimus, systemic and topical steroids he started ECP with some improvement but without remission. He was still on tacrolimus and steroids when 11 months post-transplantation he had severe worsening of his skin rash with generalized erythroderma and desquamation ranked as stage 4 and grade 4 acute GVHD of the skin. He started oral CBD 45 mg twice a day and prednisone 40 mg once a day. Skin rash and desquamation improved promptly until complete resolution. CBD was stopped 2 months later after obtaining complete remission of acute GVHD. Tacrolimus and steroids were gradually tapered off until complete cessation.

A 39 year old female with acute myeloid leukemia in first complete remission, underwent an allogeneic hematopoietic cell transplantation from a male matched sibling donor with myeloablative conditioning consisting of busulfex (12.8 mg/kg) and cyclophosphamide (120 mg/kg). Eight months post-transplantation, leukemia relapsed. She received salvage chemotherapy followed by donor lymphocyte infusion (DLI) and achieved a complete hematologic remission. One month post DLI she developed jaundice with bilirubin levels of 11.5 mg % (normal≤1 mg %) and biopsy proven late onset acute GVHD of the liver ranked as stage 3 and grade 3. She was refractory to high-dose steroids and started oral CBD 150 mg twice a day. Jaundice resolved within few days and bilirubin dropped to normal levels (0.7-1.3 mg %)). Steroids could be tapered off until complete cessation Thus reducing the therapeutically effective dose of a steroid can be a process wherein the steroid dose administered with CBD is gradually decreased over time.

The above case studies demonstrate not only that CBD treatment is effective for treatment of acute Grade 3 and Grade 4 GVHD, but that it provides complete treatment of the most severe forms of GVHD for which a cure is otherwise not possible. The present CBD treatment, unexpectedly, rendered a refractory dose of a steroid-therapeutically effective. Moreover, this examples demonstrates that CBD is effective in treatment of severe acute GVHD as it occurs in all effective organs.

Example 4: Cannabidiol (CBD) for Treatment of Severe Refractory Chronic GVHD

This example describes cases studies that show the surprising efficacy of CBD treatment of patients experiencing severe refractory chronic GVHD.

A 35 year old male with acute lymphoid leukemia in first complete remission, underwent an allogeneic hematopoietic cell transplantation from a female matched unrelated donor with myeloablative conditioning consisting of total body irradiation (12 Gray), cyclophosphamide and ATG (Fresenius, 15 mg/kg). The patient developed an overlap syndrome (concomitant acute plus chronic GVHD features) during the first month after transplantation which was treated with cyclosporine and steroids until complete remission. Immunosuppression was stopped 5 months after transplantation. Eighteen months after transplantation he developed chronic extensive GVHD with involvement of the oral cavity, eyes, liver, joints and skin. Skin involvement progressed to sclerosis. He started again cyclosporine and oral steroids with no improvement. There was no further improvement with imatinib (Gleevec). He started oral CBD, as prepared above, at 75 mg twice a day, and after several weeks of treatment he resolved his liver and oral GVHD and significantly improved skin sclerosis and joint range of motion. This outcome, unexpectedly and clearly demonstrated that CBD was absolutely necessary to render the refractory steroid therapy—effective. Unexpectedly, Prednisone effective therapeutic dose was tapered off up to 7.5-10 mg QD (20-50% reduction in the steroid's dose).

A 35 year old female with acute myeloid leukemia in second complete remission underwent an allogeneic hematopoietic cell transplantation from a matched female sibling donor with myeloablative conditioning consisting of busulfex (12.8 mg/kg) and cyclophosphamide (120 mg/kg). The patient experienced relapse in the central nervous system and breasts 12 months after transplantation, received chemo-radiotherapy and achieved complete remission. Shortly after remission, she developed chronic extensive GVHD with severe involvement of the eyes, joint and skin. Skin involvement progressed to severe sclerosis with limited range of motion of the joints. She was unresponsive to cyclosporine and oral steroids and therefore they were stopped after few months. She started oral CBD 75 mg BID and after several months she had significant improvement of her skin and joints range of motion. Interestingly and unexpectedly, these clinical outcomes show that CBD has a significant therapeutic effect in treating GVHD with and without steroid treatment.

Example 5: Cannabidiol (CBD) Reduced the Actual Effective Dose of Steroids and Renders Ineffective Dose, Therapeutically Effective 63 year old female with secondary acute myeloid leukemia in 1$^{st}$ complete remission, underwent and allogeneic hematopoietic cell transplantation from a male matched unrelated donor with a myeloablative conditioning consisting of fludarabine (160 mg/m$^2$), busulfex (12.8 mg/kg) and ATG (Fresenius, 15 mg/kg). Eleven months after transplantation she developed jaundice with bilirubin level of 4.2 mg % and biopsy proven late onset acute GVHD of the liver ranked as stage 2 and grade 3. She started tacrolimus and high-dose steroids and had a partial response for a short period of time. Two months later (13 months post transplantation), while still given tacrolimus and steroids she had an upsurge in bilirubin to 8.5 mg %, ranked as stage 3 and grade 3 acute GVHD of the liver. She started oral CBD 150 mg BID. Jaundice resolved gradually and bilirubin dropped to normal levels. Steroids could be tapered off to a low dose of 7.5 mg QD.

A 58 year old male with refractory follicular lymphoma underwent an allogeneic hematopoietic cell transplantation from a male matched unrelated donor with a reduced intensity conditioning consisting of fludarabine (150 mg/m$^2$), melphalan (100 mg/m$^2$) and ATG (Fresenius 15 mg/kg) and achieved a complete remission. Two years later he relapsed and received salvage immune-chemotherapy with bendamustine and rituximab followed by DLI and achieved a complete remission. One month later he was admitted with severe late onset acute GVHD with skin (rash) and upper (nausea and vomiting) plus lower gastrointestinal involvement (bloody diarrhea, crampy abdominal pain and severely inflamed and ulcerated mucosa). Biopsy proven GVHD was ranked as stage 3 of the skin and stage 4 and grade 4 acute GVHD of the GIT. He started cyclosporine and high-dose steroids. Despite skin response, GVHD of the GIT was refractory to prolonged systemic treatment of steroids. He started oral CBD 150 mg BID, symptoms improved gradually and a very good partial response (VGPR) was attained to the steroids. Prednisone was tapered off to 20 mg QD (40%)—found to be therapeutically effective. Two months later diarrhea resumed following discontinuing CBD without doctors' approval. A second VGPR was obtained upon renewal of methylprednisolone 0.5 mg/kg QD and CBD 150 mg BID.

What is claimed is:

1. A method for enhancing the therapeutic effect of a steroid in a subject afflicted Graph-Versus-Host Disease (GVHD), comprising administering to said subject for at least 20 days: (A) said steroid; and (B) a cannabidiol (CBD), (-)-7-hydroxy-CBD, (-)-CBD-7-oic acid, dimethylheptyl homologue of (-)-7-hydroxy-CBD, dimethylheptyl homologue of (-)-CBD-7-oic acid or any combination thereof, wherein said (B) is non-psychoactive, thereby enhancing the therapeutic effect of a steroid in a subject afflicted with inflammation.

2. The method of claim 1, wherein said enhancing the therapeutic effect of said steroid in said subject comprises reducing a side effect associated with said steroid.

3. The method of claim 1, wherein said enhancing the therapeutic effect of a steroid comprises rendering a refractory steroid dose a therapeutically effective dose.

4. The method of claim 1, wherein said enhancing the therapeutic effect of said steroid comprises reducing the effective dose of said steroid.

5. The method of claim 1, wherein said steroid, said CBD, said (-)-7-hydroxy-CBD, (-)-CBD-7-oic acid, dimethylheptyl homologue of (-)-7-hydroxy-CBD, dimethylheptyl homologue of (-)-CBD-7-oic acid or any combination thereof, or any combination thereof is administered systemically.

6. The method of claim 1, wherein said steroid, said CBD, said (-)-7-hydroxy-CBD, (-)-CBD-7-oic acid, dimethylheptyl homologue of (-)-7-hydroxy-CBD, dimethylheptyl homologue of (-)-CBD-7-oic acid, or any combination thereof is administered orally or topically.

7. The method of claim 1, wherein the CBD, or said (-)-7-hydroxy-CBD, (-)-CBD-7-oic acid, dimethylheptyl homologue of (-)-7-hydroxy-CBD, dimethylheptyl homologue of (-)-CBD-7-oic acid or any combination thereof, is administered daily in doses of between 5 mg to 600 mg.

8. The method of claim 1, wherein said enhancing the therapeutic effect of a steroid comprises converting a subject refractory to said steroid to a subject responsive to said steroid.

9. The method of claim 8, wherein said steroid, said CBD, said (-)-7-hydroxy-CBD, (-)-CBD-7-oic acid, dimethylheptyl homologue of (-)-7-hydroxy-CBD, dimethylheptyl homologue of (-)-CBD-7-oic acid or any combination thereof, or any combination thereof is administered systemically.

10. The method of claim 8, wherein said steroid, said CBD, said (-)-7-hydroxy-CBD, (-)-CBD-7-oic acid, dimethylheptyl homologue of (-)-7-hydroxy-CBD, dimethylheptyl homologue of (-)-CBD-7-oic acid, or any combination thereof is administered orally or topically.

11. The method of claim 8, wherein the CBD, or said (-)-7-hydroxy-CBD, (-)-CBD-7-oic acid, dimethylheptyl homologue of (-)-7-hydroxy-CBD, dimethylheptyl homologue of (-)-CBD-7-oic acid or any combination thereof, is administered daily in doses of between 5 mg to 600 mg.

12. The method of claim 8, wherein said GVHD is scleroderma.

13. The method of claim 1, wherein said subject has been treated with said steroid for at least 1 month before said administering.

14. The method of claim 3, wherein said subject has been treated with said steroid for at least 1 month before said administering.

15. The method of claim 8, wherein said subject has been treated with said steroid for at least 1 month before said administering.

16. The method of claim 1, wherein said GVHD is scleroderma.

* * * * *